United States Patent
More et al.

(10) Patent No.: US 8,447,400 B2
(45) Date of Patent: *May 21, 2013

(54) SYSTEMS AND METHODS FOR USE BY AN IMPLANTABLE MEDICAL DEVICE FOR CONTROLLING MULTI-SITE CRT PACING IN THE PRESENCE OF ATRIAL TACHYCARDIA

(75) Inventors: Rohan A. More, Glendale, CA (US); Heidi Hellman, Los Angeles, CA (US); Eliot L. Ostrow, Sunnyvale, CA (US); Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 386 days.

This patent is subject to a terminal disclaimer.

(21) Appl. No.: 12/822,983

(22) Filed: Jun. 24, 2010

(65) Prior Publication Data

US 2011/0319951 A1    Dec. 29, 2011

(51) Int. Cl.
*A61N 1/368* (2006.01)

(52) U.S. Cl.
USPC ............................................................ 607/14

(58) Field of Classification Search
None
See application file for complete search history.

(56) References Cited

U.S. PATENT DOCUMENTS

| | | | |
|---|---|---|---|
| 4,974,589 A | 12/1990 | Sholder | |
| 5,441,523 A | 8/1995 | Nappholz | |
| 5,591,214 A | 1/1997 | Lu | |
| 6,181,968 B1 | 1/2001 | Limousin | |
| 6,477,420 B1 * | 11/2002 | Struble et al. | 607/14 |
| 6,512,952 B2 | 1/2003 | Stahmann et al. | |
| 6,628,988 B2 | 9/2003 | Kramer et al. | |
| 6,643,546 B2 | 11/2003 | Mathis et al. | |
| 6,671,548 B1 * | 12/2003 | Mouchawar et al. | 607/14 |
| 6,810,283 B2 | 10/2004 | Suribhotla et al. | |
| 7,146,213 B1 | 12/2006 | Levine | |
| 7,158,829 B1 | 1/2007 | Levine | |
| 7,174,210 B1 | 2/2007 | Levine | |
| 7,184,834 B1 | 2/2007 | Levine | |
| 7,187,972 B1 | 3/2007 | Fain et al. | |
| 7,212,855 B1 * | 5/2007 | Kroll et al. | 607/4 |

(Continued)

FOREIGN PATENT DOCUMENTS

| | | |
|---|---|---|
| WO | 2006118852 A2 | 11/2006 |
| WO | 2006118852 A3 | 11/2006 |
| WO | 2006118854 A2 | 11/2006 |
| WO | 2006118854 A3 | 8/2007 |

OTHER PUBLICATIONS

Levine, P.A. et al., "Implementation of automatic mode switching in Pacesetter's Trilogy DR+ and Affinity DR pulse generators," Herzschr Elektrophys. 1999;10(Suppl):1/46-1/57.

*Primary Examiner* — Kennedy Schaetzle

(57) ABSTRACT

Systems and methods are provided for use by implantable medical devices equipped to deliver multi-site left ventricular (MSLV) pacing. MSLV is associated with a relatively long post-ventricular atrial blanking (PVAB) period that might limit the detection of pathologic rapid organized atrial tachycardias (OAT). In one example, MSLV cardiac resynchronization therapy (CRT) pacing is delivered within a tracking mode. A possible atrial tachycardia is detected based on the atrial rate exceeding an atrial tachycardia assessment rate (ATAR) threshold. The device then switches to single-site LV pacing, thereby effectively shortening the PVAB to detect additional atrial events that might otherwise be obscured, and thereby permitting the device to more reliably distinguish organized atrial tachycardias (such as atrial flutter) from sinus tachycardia. The device may also employ an automatic mode switch (AMS) threshold that is set higher than the ATAR threshold for use in switching from tracking modes to non-tracking modes.

21 Claims, 9 Drawing Sheets

U.S. PATENT DOCUMENTS

| | | |
|---|---|---|
| 7,248,925 B2 | 7/2007 | Bruhns et al. |
| 7,272,438 B2 | 9/2007 | Kroll et al. |
| 7,398,123 B1 | 7/2008 | Levine |
| 7,437,190 B1 | 10/2008 | Hoberman et al. |
| 7,537,569 B2 | 5/2009 | Sarkar et al. |
| 7,590,446 B1 | 9/2009 | Min et al. |
| 7,653,436 B2 | 1/2010 | Schecter |
| 7,805,192 B2 * | 9/2010 | Stahmann et al. ............... 607/9 |
| 8,160,700 B1 * | 4/2012 | Ryu et al. ........................ 607/9 |
| 2003/0208239 A1 * | 11/2003 | Lu ..................................... 607/9 |
| 2005/0125041 A1 | 6/2005 | Min et al. |
| 2006/0247547 A1 | 11/2006 | Sarkar et al. |
| 2006/0247548 A1 | 11/2006 | Sarkar et al. |
| 2006/0247698 A1 * | 11/2006 | Burnes et al. .................... 607/9 |
| 2007/0156191 A1 * | 7/2007 | Kroll et al. ....................... 607/9 |
| 2007/0179390 A1 | 8/2007 | Schecter |
| 2008/0306567 A1 | 12/2008 | Park et al. |
| 2009/0182390 A1 * | 7/2009 | Hess .............................. 607/17 |
| 2009/0281587 A1 | 11/2009 | Pei |
| 2009/0287268 A1 * | 11/2009 | Nabutovsky et al. ........... 607/14 |
| 2009/0299423 A1 | 12/2009 | Min |
| 2010/0016909 A1 * | 1/2010 | Gachiengo et al. .............. 607/4 |
| 2010/0042174 A1 * | 2/2010 | Koh et al. ....................... 607/19 |
| 2010/0145405 A1 | 6/2010 | Min et al. |
| 2011/0319953 A1 * | 12/2011 | Reed et al. ..................... 607/14 |

* cited by examiner

SYSTEMS AND METHODS FOR USE BY AN IMPLANTABLE MEDICAL DEVICE FOR CONTROLLING MULTI-SITE CRT PACING IN THE PRESENCE OF ATRIAL TACHYCARDIA

FIELD OF THE INVENTION

The invention generally relates to implantable cardiac rhythm management devices equipped with multi-pole left ventricular (LV) leads and in particular, to techniques for controlling cardiac resynchronization therapy (CRT) in the presence of a possible atrial tachycardia for use with such devices.

BACKGROUND OF THE INVENTION

An implantable cardiac rhythm management device is a type of implantable medical device (IMD) that delivers therapy to the heart of a patient in which the device is implanted. For example, a pacemaker recognizes various cardiac arrhythmias and delivers electrical pacing pulses to the heart in an effort to remedy the arrhythmias. An implantable cardioverter/defibrillator (ICD) additionally or alternatively recognizes ventricular tachycardia (VT) and ventricular fibrillation (VF) and delivers electrical shocks or other therapies to terminate these ventricular tachyarrhythmias. At least some pacemakers and ICDs are also equipped to deliver CRT to the heart of the patient. Briefly, CRT seeks to normalize the dyssynchronous cardiac electrical activation and resultant dyssynchronous contractions associated with congestive heart failure (CHF) by delivering synchronized pacing stimulus to both sides of the left ventricle using left ventricular (LV) and right ventricular (RV) leads. The stimulus is synchronized so as to improve overall cardiac function. This may have the additional beneficial effect of reducing the susceptibility to life-threatening tachyarrhythmias. CRT-D devices are implantable devices equipped to provide CRT along with defibrillation capability.

CRT and related therapies are discussed in, for example, U.S. Pat. No. 6,643,546 to Mathis et al., entitled "Multi-Electrode Apparatus and Method for Treatment of Congestive Heart Failure"; U.S. Pat. No. 6,628,988 to Kramer et al., entitled "Apparatus and Method for Reversal of Myocardial Remodeling with Electrical Stimulation"; and U.S. Pat. No. 6,512,952 to Stahmann et al., entitled "Method and Apparatus for Maintaining Synchronized Pacing". See, also, U.S. Patent Application No. 2008/0306567 of Park et al., entitled "System and Method for Improving CRT Response and Identifying Potential Non-Responders to CRT Therapy" and U.S. Patent Application No. 2007/0179390 of Schecter, entitled "Global Cardiac Performance."

For the purposes of controlling CRT or for detecting and responding to various arrhythmias, the heart rate of the patient is tracked by examining electrical signals that result in the contraction and expansion of the chambers of the heart. The contraction of atrial muscle tissue is triggered by the electrical depolarization of the atria, which is manifest as a P-wave in a surface electrocardiogram (ECG) and as a rapid deflection (intrinsic deflection) in an intracardiac electrogram (IEGM). The contraction of ventricular muscle tissue is triggered by the depolarization of the ventricles, which is manifest on the surface ECG by an R-wave (also referred to as the "QRS complex") and as a large rapid deflection (intrinsic deflection) within the IEGM. The electrical activation detected by the pacemaker on either the atrial or ventricular channel is the intrinsic deflection arising from that specific chamber. Repolarization of the ventricles is manifest as a T-wave in the surface ECG and a corresponding deflection in the IEGM. A similar depolarization of the atrial tissue usually does not result in a detectable signal within either the surface ECG or the IEGM because it coincides with, and is obscured by, the R-wave. Note that the terms P-wave, R-wave and T-wave initially referred only to features of a surface ECG. Herein, however, for the sake of brevity and generality, the terms are used to refer to the corresponding signals as sensed internally. Also, where an electrical signal is generated in one chamber but sensed in another, it is referred to herein, where needed, as a "far-field" signal. Hence, an R-wave sensed in the atria is a far-field R-wave (FFRW). The misidentification of an FFRW as a P-wave on the atrial channel is referred to herein as FFRW oversensing.

The sequence of electrical events that represent P-waves, followed by R-waves (or QRS complexes), followed by T-waves can be detected within IEGM signals sensed using pacing leads implanted inside the heart. To help prevent misidentification of electrical events and to more accurately detect the heart rate, the stimulation device employs one or more refractory periods and blanking periods. Within a refractory period, the device does not process electrical signals during a predetermined interval of time—either for all device functions (an absolute refractory period) or for selected device functions (a relative refractory period). As an example of a refractory period, upon delivery of a V-pulse to the ventricles, a post-ventricular atrial refractory period (PVARP) is applied to an atrial sensing channel. A first portion of the PVARP comprises a post-ventricular atrial blanking (PVAB) interval (which can also be referred to as an absolute refractory period). The PVAB is primarily provided to prevent the device from erroneously responding to FFRWs on the atrial channel. The PVARP concludes with a relative refractory period during which the pacemaker ignores all signals detected on the atrial channel as far as the triggering or inhibiting of pacing functions is concerned, but not for other functions, such as detecting rapid atrial rates or recording diagnostic information.

Accurate detection of atrial heart rates is required, for example, for the purposes of enabling an automatic mode switch (AMS) wherein the pacemaker switches from a tracking mode such as a DDD to a nontracking mode such as VDI or DDI. More specifically, the pacemaker compares the atrial rate against an atrial tachycardia detection rate (ATDR) threshold and, if it exceeds the threshold, the pacemaker switches from the tracking mode to the nontracking mode. The ATDR threshold is typically set to, e.g. 180 beats per minute (bpm) although this is a programmable value that the physician can select based on the evaluation of the patient. As such, the ATDR can be employed both as a threshold for detecting atrial tachycardia and as a threshold for mode switching. (In some devices, a separate maximum tracking rate (MTR) is specified, which is at least 20 bpm less than the ATDR.)

Note that DDD, VDI, VVI and DDI are standard device codes that identify the mode of operation of the device. The first letter represents the chamber into which a pacing stimulus is delivered (A=atrium, V=ventricle and D=dual or both). The second letter represents that chamber in which sensing or detection can occur with the same interpretation as for the first position. The third position refers to the way the pulse generator responds to a sensed event (I=inhibited where a sensed signal inhibits the delivery of an output pulse to that chamber, T=triggered where a sensed signal triggers delivery of an output pulse. In the third position, D still means dual but refers to dual modes of response). DDD indicates a device that senses and paces in both the atria and the ventricles and is capable of both triggering and inhibiting functions based upon events sensed in the atria and the ventricles. In DDD, a sensed atrial event (P wave) will inhibit the output to the atrial channel but trigger an output to the ventricular channel after a programmable delay. If an R wave is not sensed within the triggered interval, a ventricular output will be delivered at the end of the interval. This is the technologic equivalent of the physiologic PR interval. VVI indicates that the device is capable of pacing and sensing only in the ventricles. The mode of response to a sensed event is inhibition of the ventricular output and resetting of the basic timing interval. VDI is identical to VVI except that it is also capable of sensing intrinsic atrial activity although it can only pace in the ventricle. DDI is identical to DDD except that the device is only capable of inhibiting pacing based upon sensed events, rather than triggering on sensed events. As such, the DDI mode is a nontracking mode precluding it from triggering ventricular outputs in response to sensed atrial events but capable of pacing in both the atrium and ventricle. Numerous other device modes of operation are possible, each represented by standard abbreviations of this type.

Thus, in a DDD pacing system, AMS recognizes when the patient is in an atrial tachycardia such as atrial fibrillation (AF) and switches from a tracking mode to a nontracking mode to prevent the device from attempting to track the high atrial rates associated with the pathologic atrial tachyarrhythmia (AF). Details regarding AMS may be found in the following patents: U.S. Pat. Nos. 5,441,523 and 5,591,214. See also Levine et al., "Implementation of Automatic Mode Switching in Pacesetter's Trilogy DR+ and Affinity DR Pulse Generators," Herzschr. Elektrophys. 10 (1999) 5, S46-S57. See, also, the AMS techniques described in U.S. Pat. No. 7,272,438 to Kroll et al., entitled "Mode Switching Heart Stimulation Apparatus and Method" and U.S. Pat. No. 7,187,972 to Fain et al., entitled "Bi-ventricular Pacing in the Face of Rapidly Conducting Atrial Tachyarrhythmia."

See, also, U.S. Pat. Nos. 7,146,213, 7,158,829, 7,174,210 and 7,184,834 to Levine, each entitled "Method and Apparatus for Improving Specificity of Tachycardia Detection Techniques in Dual-unipolar and Dual-Bipolar Implantable Cardiac Stimulation Systems." Also, see, U.S. Pat. No. 7,398,123 to Levine, entitled "Methods and devices for reducing the detection of inappropriate physiologic signals to reduce misdiagnosis of normal rhythms as tachyarrhythmias."

Issues can arise when CRT is delivered by a device equipped for responding to supraventricular tachyarrhythmias with AMS, particularly within devices employing quadra-pole or other multi-pole LV leads, i.e. within devices equipped to deliver multisite CRT. With Multisite LV (MSLV) CRT, pacing stimuli are selectively delivered to the LV at various locations using a set of electrodes distributed along the LV lead or on multiple LV leads in different sites. (This stimulus is synchronized with stimulus pulses delivered to the RV using, e.g., an otherwise conventional bipolar RV lead.) MSLV pacing stimuli and residual charge may be associated with complexes that can be sensed in the atria (i.e. FFRWs sensed on an atrial sensing channel). In at least some devices, due to complications involving hardware discharge and hardware limitations, the net effect during MSLV is one relatively long overall PVAB in the range of, e.g., 130-150 milliseconds (ms) This relatively long PVAB can interfere with the capability of the device to detect and respond to various organized atrial tachycardias (OATs), such as atrial flutter by blinding the system to some of the atrial events. In particular, the relatively long PVAB can prevent the device from properly distinguishing an OAT from a high sinus rate, as might occur during patient exercise, or from sinus rates that only appear to be high due to FFRW oversensing. (A state-of-the-art lead, such as the OptiSense™ lead of St Jude Medical, can help minimize FFRW oversensing, but might not eliminate the phenomenon entirely. In addition, the pulse generator may be connected to an older generation atrial lead, which does not have the same capability to minimize detection of FFRWs).

With regard to atrial flutter, the relatively long PVAB associated with MSLV could preclude detection of every other flutter wave. Circumstances can arise where the device treats this rhythm as a sinus tachycardia resulting in tracking the atrium and a sustained high ventricular paced rate that can aggravate or precipitate overt heart failure due to the sustained high rate pacing, despite any on-going CRT. Conversely, too short a PVAB can predispose the device to FFRW oversensing and inappropriate mode switching.

Accordingly, it would be desirable to provide techniques for controlling MSLV pacing, particularly in conjunction with AMS, which address these and other concerns.

SUMMARY OF THE INVENTION

In accordance with a first exemplary embodiment of the invention, methods are provided for use by implantable cardiac rhythm management devices equipped to selectively deliver MSLV pacing within a patient. In one example, MSLV pacing is delivered to the heart of the patient by the device within a tracking mode and the atrial rate of the patient is assessed. The atrial rate is compared against an atrial tachycardia assessment rate threshold (ATAR) and, if the atrial rate exceeds the ATAR threshold, the device switches from MSLV pacing to single-site LV pacing so as to shorten PVAB interval and enable recognition of organized atrial arrhythmias (OATs). (By "single-site LV pacing," it is meant that—as far as the LV is concerned—pacing stimulus is delivered only at a single site. Additional pacing stimulus might also be delivered in the RV. A typical form of "single-site LV pacing" is BiV pacing between the RV and LV.) The device also preferably compares the atrial rate against a higher AMS threshold and, if the atrial rate exceeds the AMS threshold, the device performs a mode switch to a nontracking mode.

In an illustrative CRT example, the technique is implemented by an implantable device that applies a relatively long overall PVAB during MSLV CRT, but which uses a shorter PVAB during single-site LV CRT. By switching from MSLV pacing to single-site LV pacing once the ATAR threshold has been exceeded, the device thereby shortens the PVAB, permitting the device to more reliably distinguish OATs (such as atrial flutter) from high-rate sinus rhythms or from sinus rhythms that only appear high due to FFRW oversensing. By switching to a nontracking mode above the AMS threshold, AF can thereby be detected and addressed. In at least some embodiments, if the atrial rate is above the AMS threshold, the device continues using MSLV (albeit, now in a nontracking mode rather than a tracking mode). It should be noted though that, depending upon the atrial rate and the length of the PVAB interval during MSLV, the device might not accurately detect high atrial rates during MSLV in a nontracking mode. Also, given the long PVAB associated with MSLV pacing, it can be difficult to distinguish AF from OAT while MSLV pacing continues. As such, in many cases it is preferred that MSLV be deactivated at all rates above the ATAR threshold (i.e. not merely at rates between ATAR and the AMS threshold.) As can be appreciated, a variety of variations can be implemented.

In one particular example, the ATAR threshold is set to 120 bpm. (This is the rate at which MSLV is disabled and PVAB is shortened to facilitate the detection of a possible OAT.) The higher AMS threshold (used to determine whether to switch from the tracking mode to a nontracking mode) is set to 180 bpm. That is:

ATAR threshold=a lower threshold used to disable or disengage MSLV and to shorten the PVAB to facilitate the detection of OAT; and AMS threshold=a higher threshold used to detect AT/AF and to switch from a tracking mode to a nontracking mode.

This differs from predecessor devices that use a single ATDR threshold both to detect atrial tachycardia and to trigger a mode switch.

Alternatively, one might refer to the lower ATAR threshold as a "low ATDR threshold" and the higher AMS threshold as a "high ATDR threshold." The ATAR threshold might also be referred to as an "MSLV disengagement rate" threshold. For the sake of consistency herein, and to avoid confusion with the traditional ATDR threshold, the terms "ATAR threshold" and "AMS threshold" are instead used herein. It should be appreciated that the particular choice of terminology does not affect the scope of the invention.

In the illustrative example, the device additionally employs rate stability and waveform morphology to discriminate among possible atrial rhythms, such as between OAT and AF (at rates above the AMS threshold) or between OAT and sinus rhythm (at rates below the AMS threshold but above the lower ATAR threshold.) For example, to distinguish OAT from AF at rates above the AMS threshold, the device detects a degree of stability in atrial event intervals detected on an atrial sensing channel during MSLV pacing and also detects the morphology of the atrial events. The atrial rhythm is identified as AF if either (1) the atrial intervals are significantly unstable or (2) atrial waveform morphology is not substantially consistent from one waveform to another. Otherwise, the atrial rhythm is instead identified as OAT.

Conversely, to discriminate among various atrial rhythms at rates below the AMS threshold (but above the ATAR threshold), the device first examines events on the atrial channel to detect a possible bigeminal pattern indicative of FFRW oversensing on the atrial channel. If such a bigeminal pattern is detected, the device identifies the atrial rhythm as a sinus rhythm with bigeminy and switches back to MSLV pacing. This determination can be corroborated by examining waveform morphology since the intrinsic atrial event will differ in morphology from the FFRW signal. Assuming that a bigeminal pattern is not detected, the device then examines atrial interval stability and atrial morphology to distinguish between OAT and a sinus rhythm (without bigeminy). Insofar as interval instability is concerned, in many patients atrial interval rates may vary by only a few milliseconds from cycle to cycle and so morphology may be a preferred discriminator. If OAT is detected at rates above the ATAR threshold but below the AMS threshold, the device mode switches to a nontracking mode for the duration of the OAT. Once the abnormal rhythm ends, MSLV pacing resumes in a tracking mode, such as DDD. Note also that the various techniques used for distinguishing AF, OAT, sinus rhythm, etc., are not restricted for use with MSLV techniques. Indeed, various aspects of the invention are applicable outside the scope of MSLV pacing.

In an alternative embodiment, upon the detection of OAT during single-site LV pacing (i.e. after MSLV has been disabled), the device reactivates MSLV during the OAT to improve hemodynamics while periodically switching back to single-site LV pacing with its significantly foreshortened PVAB just long enough to determine whether OAT is still present. This is preferably only performed if there is intrinsic conduction through the AV node of the heart of the patient, as indicated by 2:1 conduction or, at lower rates, 1:1 conduction (with pacing). Thus, for example, the device examines atrial and ventricular depolarization patterns to detect a 2:1 or 1:1 conduction pattern indicative of intrinsic AV conduction and, in response, the device re-activates MSLV pacing in a triggered pacing mode (so long as a ventricular triggered rate is below the AMS threshold). The device then periodically engages AMS and temporarily switches back to single-site LV pacing (for, e.g., three cycles) to determine if OAT is still present. If OAT is no longer present the device exits AMS using otherwise standard exit criteria and, when tracking mode pacing is resumed, if atrial rate is below the ATAR threshold, then MSLV pacing is resumed. Note, also, that the intervals between OAT searches preferably increase so long as OAT continues, such as by increasing from once every minute to once every two minutes (then once every three minutes, once every five minutes, and so on.)

In another alternative embodiment, upon the detection of OAT during single-site LV pacing, the device reactivates MSLV during the OAT and remains in the MSLV mode and, eventually, the OAT spontaneously terminates. That is, in this alternative embodiment, there are no periodic searches for OAT. In still other embodiments, arrhythmia discriminators are not employed until the atrial rate exceeds the AMS threshold.

In yet another alternative embodiment, the device switches to single-site LV pacing whenever the atrial rate exceeds the ATAR threshold and continues to use single-site LV pacing at all rates above the ATAR threshold (including rates above the higher AMS threshold.) In this example, the AMS threshold is still used to control switching from tracking to nontracking modes but has no effect on whether single-site LV or MSLV pacing is delivered.

BRIEF DESCRIPTION OF THE DRAWINGS

The above and further features, advantages and benefits of the present invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System/Method

Figure 1:
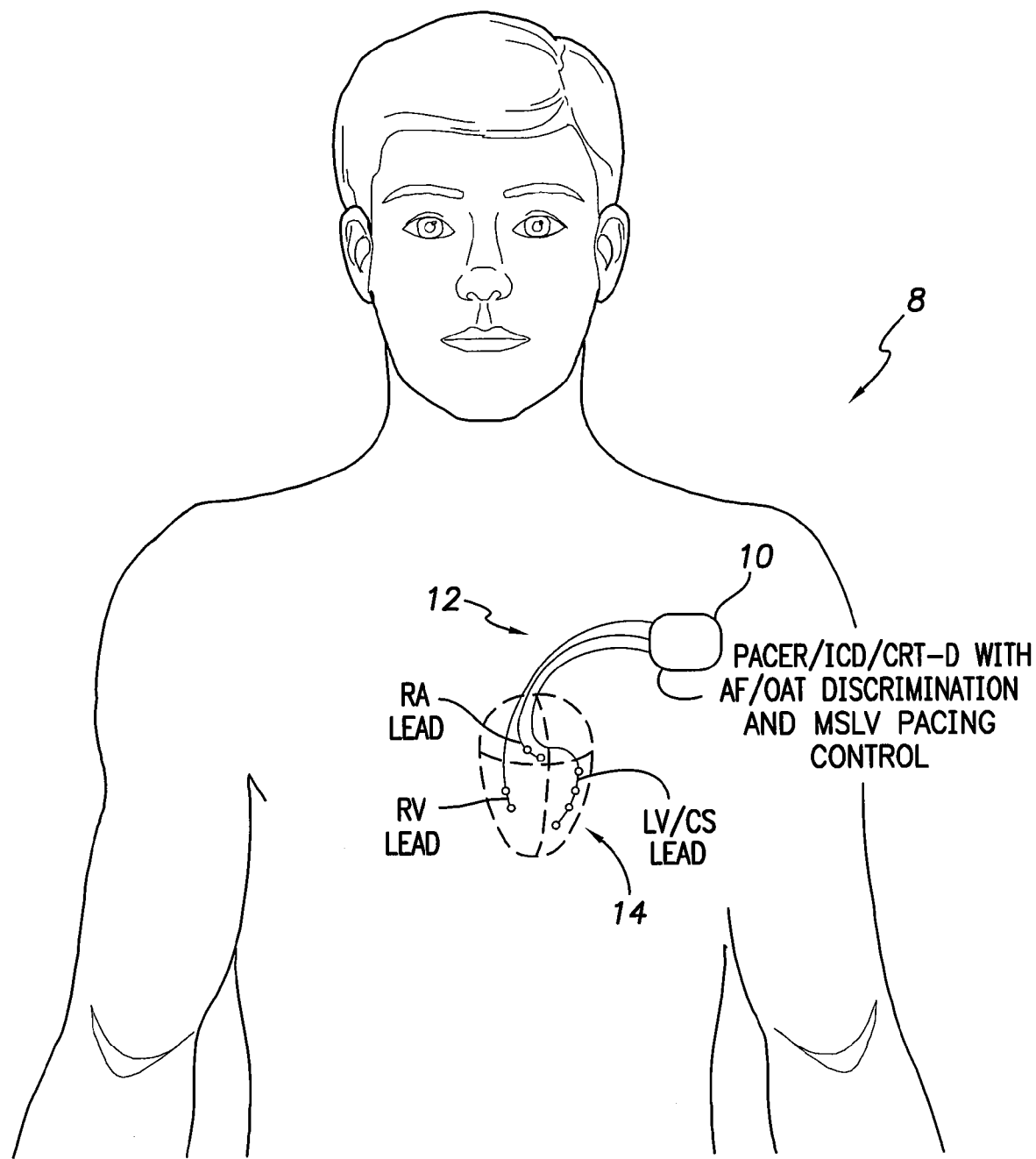
FIG. 1 illustrates pertinent components of a pacer/ICD or CRT-D equipped with a system for discriminating OAT from AF and for controlling MSLV CRT pacing based on atrial rate and other factors.

FIG. 1 illustrates an implantable medical system 8 capable of delivering MSLV CRT or other forms of cardiac pacing therapy. The medical system includes a pacer/ICD or CRT-D 10 or other cardiac rhythm management device equipped with a set of cardiac leads 12 implanted on or within the heart of the patient, including a multi-pole LV lead implanted via the coronary sinus (CS). In FIG. 1, a stylized representation of the set of leads is provided. To illustrate the multi-pole configuration of the LV lead, four electrodes 14 are shown distributed along the LV lead. The RV and RA leads are each shown with a pair of electrodes, though each of those leads may include additional electrodes as well, such as additional electrode pairs and shocking coils. Still further, the LV lead can also include a shocking coil and one or more left atrial (LA) electrodes mounted on or in the LA via the CS. See FIG. 8 for a more complete and accurate illustration of various exemplary leads.

As will be explained, the device is equipped to detect a possible atrial tachycardia while CRT is delivered and to selectively switch between MSLV CRT pacing and single-site LV CRT (i.e. otherwise conventional BiV pacing in the RV and LV with CRT delivered) pacing in response to the possible atrial tachycardia. The device is also equipped to identify the particular atrial tachycardia (if any) and to perform a variety of responsive functions, such as to initiate therapy in response to the particular atrial tachycardia, record diagnostic information and/or generate warning signals in response to the atrial tachycardia.

In addition, depending upon the particular capabilities of device 10, the system can perform a wide range of other cardiac rhythm management functions, such as detecting and responding to various ventricular arrhythmias such as VF, delivering defibrillation shocks in response to VF, and the like. These and other functions are described below with reference to FIG. 9. The following descriptions will instead focus on the detection and discrimination of atrial tachycardias and the control of single-site LV pacing vs. MSLV pacing.

Figure 2:
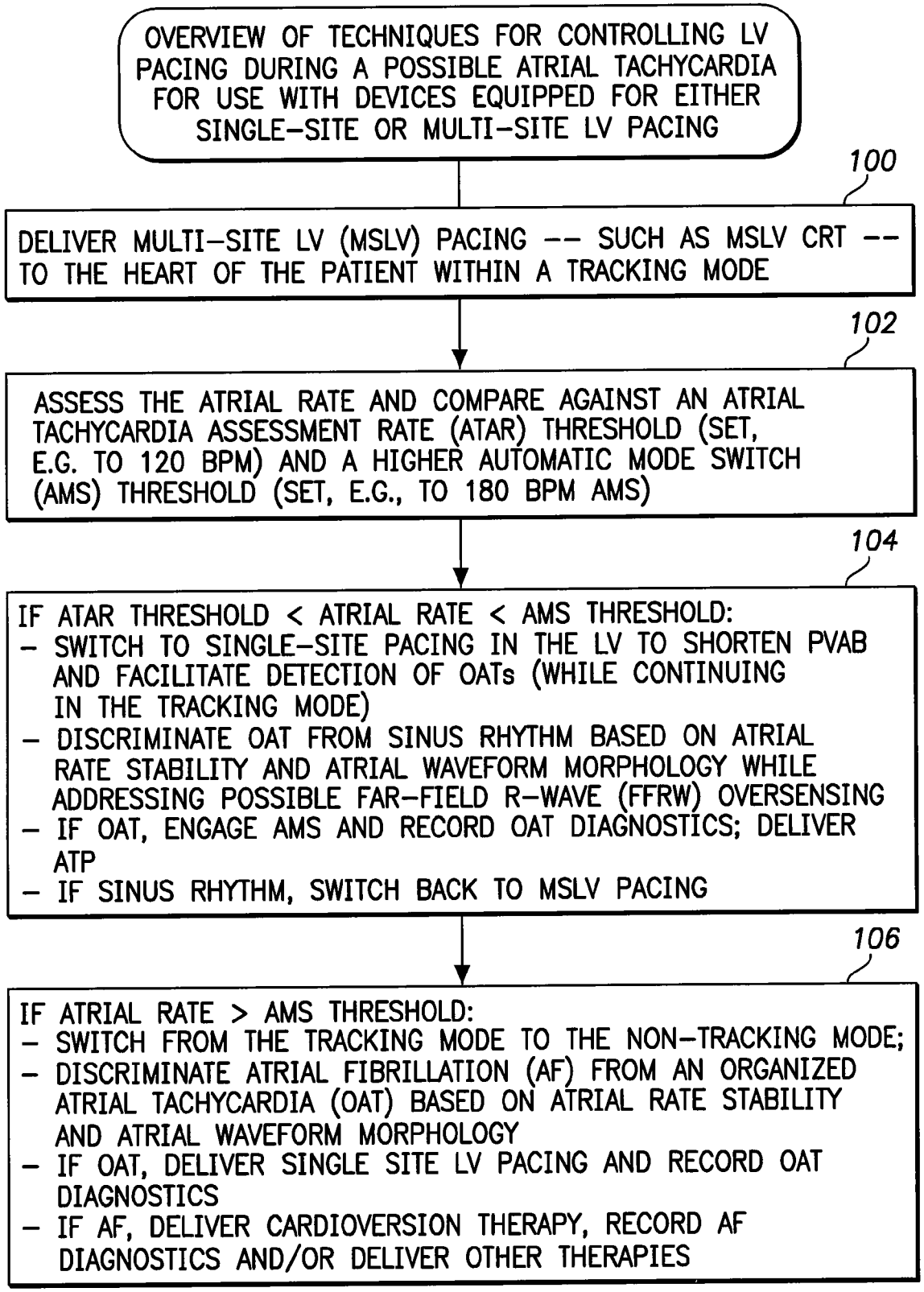
FIG. 2 provides a broad overview of a method for detecting and distinguishing OAT/AF and for controlling MSLV CRT that can be performed by the system of FIG. 1, wherein separate thresholds are employed for detecting a possible atrial tachycardia and for controlling mode switching and wherein MSLV is selectively disengaged based on the atrial rate.

FIG. 2 broadly summarizes a general technique for controlling single-site LV/MSLV pacing during a possible atrial tachycardia that may be performed by the pacer/ICD/CRT-D of FIG. 1 or other suitably equipped systems. Beginning at step 100, the device delivers MSLV pacing—such as MSLV CRT—to the heart of the patient within a tracking mode, such as within the DDD mode. At step 102, the device assesses the atrial rate and compares it against the ATAR threshold (set, e.g. to 120 bpm) and to the higher AMS threshold (set, e.g., to 180 bpm). Note that both the ATAR threshold and the AMS threshold can be programmable values. In one example, the ATAR threshold is programmed in the range of 110-130 bpm and the AMS threshold is programmed in the range of 170 bpm to 300 bpm. These are just examples.

At step 104, if ATAR threshold<atrial rate<AMS threshold, then the device (1) switches to single-site pacing in the LV while continuing in the tracking mode and thereby reduces the effective overall PVAB length to permit detection of events on the atrial channel that might otherwise be blanked; and (2) discriminates OAT from sinus rhythm based on atrial rate stability and atrial waveform morphology while addressing possible FFRW oversensing. Techniques for discriminating OAT from sinus rhythm based on rate stability and waveform morphology while address FFRW oversensing will be described below. If OAT is identified, the device then engages AMS (i.e. the device switches to a nontracking mode) and records OAT diagnostics. If a sinus rhythm is instead identified (i.e. there is no ongoing atrial tachycardia), the device simply switches back to MSLV pacing.

At step 106, if AMS threshold<atrial rate, the device: (1) switches from the tracking mode to a nontracking mode (such as DDI) while (in some examples) delivering MSLV pacing; and (2) discriminates AF from OAT based, e.g., on atrial rate stability and atrial waveform morphology. Techniques for discriminating AF from OAT based on rate stability and waveform morphology will be described below. If OAT is identified, the device then switches to single site LV pacing and records OAT diagnostics for subsequent clinician review. Antitachycardia pacing (ATP) can also be delivered in response to OAT. If AF is instead identified, the device delivers AF therapy and/or records AF diagnostics. AF therapy can include the delivery of cardioversion shocks to the atria, if the system is so equipped and if the clinician has programmed the device to deliver such shocks. Note that, depending upon the implementation, the device might deliver MSLV pacing at rates above the AMS threshold or it might deliver single-site LV pacing. For example, the device can engage AMS above the AMS threshold but with rate response turned on. In some circumstances, it might be possible for the ventricular pacing rate to become fast enough such that—if MSLV pacing is delivered—the long PVAB associated with MSLV would make it difficult to properly assess the atrial rate, and hence single-site pacing would be preferable at those high rates.

In the following section, these general techniques are described in greater detail.

Exemplary Techniques with Interval Stability/Morpholoqy Discrimination

Figure 3:
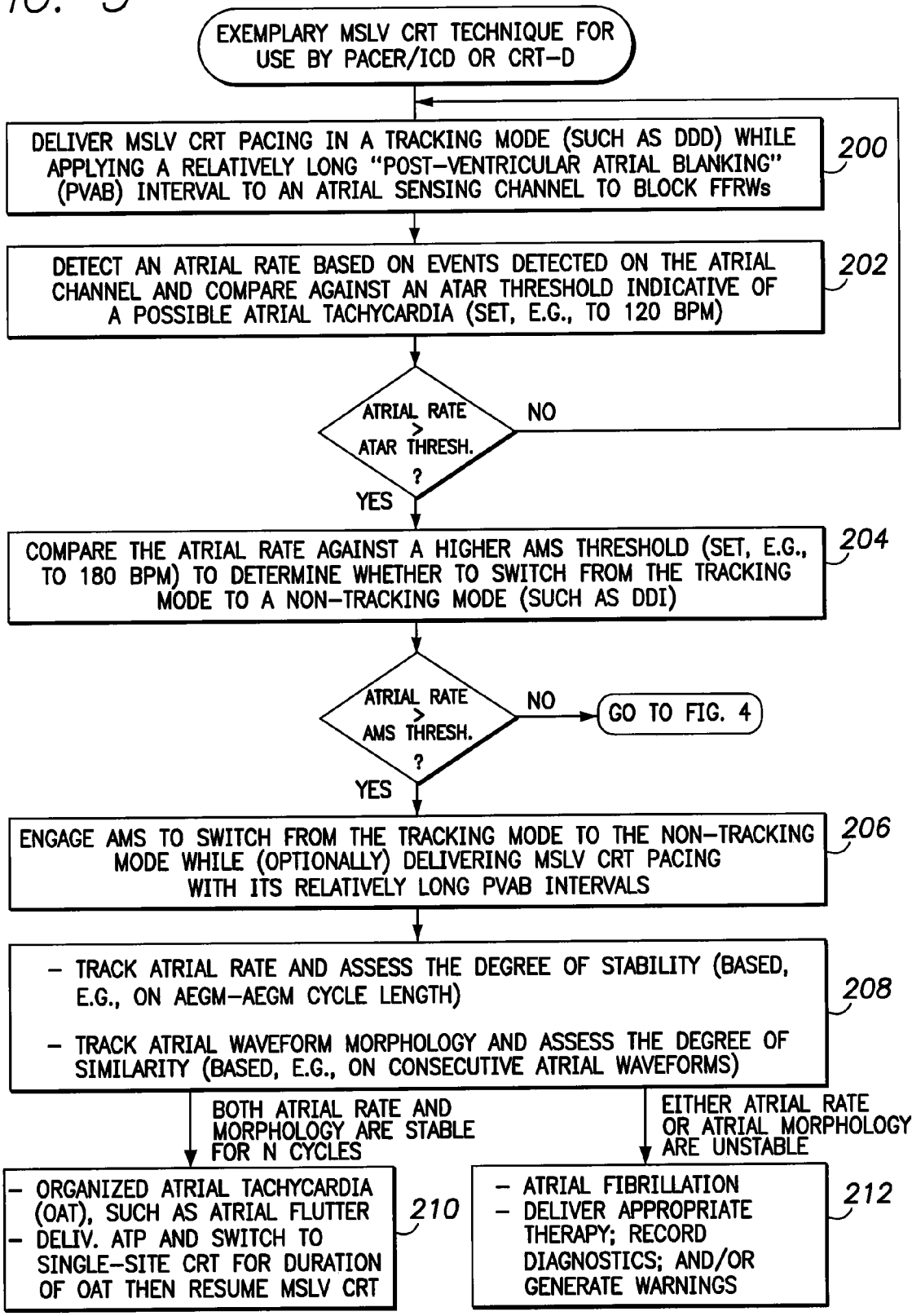
FIG. 3 is a flow chart illustrating an illustrative MSLV CRT control technique in accordance with the general technique of FIG. 2, wherein interval stability and waveform morphology are employed to discriminate OAT from AF at high atrial rates.
Figure 4:
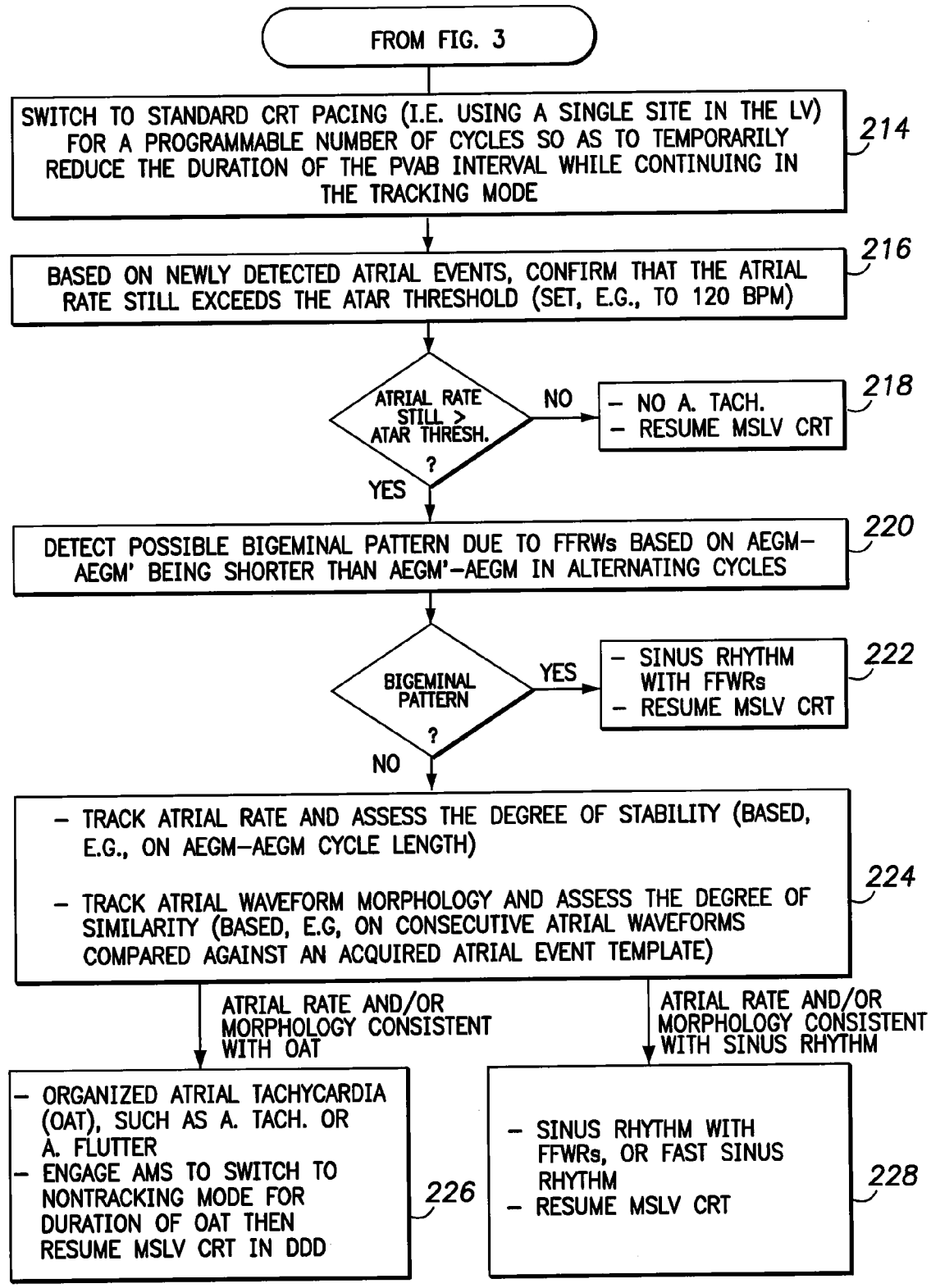
FIG. 4 is a continuation of the flow chart of FIG. 3 wherein interval stability and waveform morphology are employed to discriminate OAT from sinus rhythm at somewhat lower atrial rates.

FIGS. 3 and 4 illustrate a technique wherein MSLV is selectively disengaged upon detection of a possible atrial tachycardia and steps are taken to discriminate AF from OAT based on atrial interval stability and morphology. Briefly, if the rhythm is stable Atrial Sensed (AS)—Ventricular Paced (VP) at or above a programmable ATAR threshold value (e.g. 120 bpm or 500 ms) for a programmable number of cycles "X", the device labels this rhythm as possible atrial tachycardia. (The programmable number of cycles X might be set, e.g., to eight or to any other programmable value within a predetermined range from, e.g., three to fifty. Note that a relatively large number of cycles can have the effect of functionally filtering out brief non-sustained episodes.) The device then suspends MSLV in favor of a single LV pacing site. This will shorten the longer PVAB by eliminating the multiple sequential LV pacing stimuli for another programmable number of cycles. (Given the initial screen of X number of cycles before disabling MSLV with its accompanied cumulative PVAB, the device might use 3-5 cycles here, as the device is already primed to look for intrinsic events now that the PVAB has been shortened.) If a second P-wave is detected (this could be a FFRW), the device then measures the interval stability between successive P-waves. If the atrial rhythm demonstrates interval stability (which should be within a tolerance of 25-50 ms), the rhythm is still labeled a possible atrial tachycardia.

A second criterion the device exploits is morphology discrimination as applied to the atrium. Note that this does not need to be the same morphology as the sinus Atrial EGM (AEGM) and as such, a prior sinus AEGM template is not required. (Note that the term "P-wave" refers to atrial depolarization as recorded on a surface ECG; whereas the AEGM refers to the corresponding signals recorded inside the heart and these are what the implantable device utilizes.) With a stable AEGM-AEGM interval, the algorithm acquires a template for the atrial activity. If, on the next consecutive "n" cycles, the morphology template is stable (or stable within n cycles out of m cycles, e.g. 5 out of 8 complexes), the rhythm is labeled OAT and, depending upon the atrial rate, AMS is engaged. The n and m values are programmable. "Stability" may be defined relative to a match score. In one example, the match score must exceed 60% (also a programmable value) in 5 out of 8 consecutive complexes for the rhythm to be labeled OAT. Using the morphology criteria (and presuming a rapid rate such that the FFRW is almost equidistant between the two true P-waves), the atrial morphology will be different between the true P-wave and the FFRW. Note also that, for a diagnosis of an OAT to be present, both criteria should be met: interval stability and morphology stability on the atrial channel. In the presence of an OAT that is sufficiently fast to engage AMS, MSLV pacing is suspended in favor of standard CRT pacing (RV and a single LV pacing site). Once the rhythm ends allowing exit from AMS and restoration of DDD pacing, MSLV pacing is restored.

These techniques are illustrated in FIG. 3. Beginning at step 200, the device delivers MSLV CRT pacing in a tracking mode (such as DDD) while applying a relatively long PVAB interval to an atrial sensing channel to, e.g., block FFRWs. Since V-pulses are delivered at multiple sites in the LV using the multi-pole LV lead, the PVAB applied to the atrial channel during MSLV is relatively long (e.g. in the range of 125-170 ms and, nominally 150 ms) as compared to the length of a PVAB when using single-site LV pacing (e.g. about 70 ms).

In accordance with CRT, the V-pulses are selectively delivered to both the RV and the LV subject to a possible VV delay intended to improve hemodynamics. Techniques for determining suitable AV delays and VV delays are described, e.g., in the following patents and patent applications: U.S. patent application Ser. No. 10/703,070, filed Nov. 5, 2003, entitled "Methods for Ventricular Pacing"; U.S. patent application Ser. No. 10/974,123, filed Oct. 26, 2004; U.S. patent application Ser. No. 10/986,273, filed Nov. 10, 2004; U.S. patent application Ser. No. 10/980,140, filed Nov. 1, 2004; U.S. patent application Ser. No. 11/129,540, filed May 13, 2005; U.S. patent application Ser. No. 11/952,743, filed Dec. 7, 2007.

See, also, U.S. patent application Ser. No. 12/328,605, filed Dec. 4, 2008, entitled "Systems and Methods for Controlling Ventricular Pacing in Patients with Long Intra-Atrial Conduction Delays" and U.S. patent application Ser. No. 12/132, 563, filed Jun. 3, 2008, entitled "Systems and Methods for determining Intra-Atrial Conduction Delays using Multi-Pole Left Ventricular Pacing/Sensing Leads." See, further, U.S. Pat. No. 7,248,925, to Bruhns et al., entitled "System and Method for Determining Optimal Atrioventricular Delay based on Intrinsic Conduction Delays." At least some of the techniques are implemented within the QuickOpt™ systems of St. Jude Medical.

At step 202, the device detects an atrial rate (i.e. the AS-AS rate) based on events detected on the atrial channel and compares the rate against an ATAR threshold indicative of a possible atrial tachycardia (set, e.g., to 120 bpm). For example, the device detects the atrial rate over some predetermined number of cycles and, assuming that the rate is sufficiently stable to provide an adequate estimate of the atrial rate, the device compares that rate against the ATAR threshold. As already explained, this threshold differs from some conventional ATDR thresholds, which are used to both detect atrial tachycardia and trigger a mode switch. The conventional ATDR threshold is typically set much higher, usually about 180 bpm.

Assuming that the atrial rate exceeds the ATAR threshold, then, at step 204, the device compares the atrial rate against a higher AMS threshold (set, e.g., to 180 bpm) to determine whether to engage AMS, i.e. to switch from the tracking mode to a nontracking mode such as DDI. If the atrial rate also exceeds this higher threshold, then the remaining steps of FIG. 3 are performed. Otherwise, processing continues with the steps of FIG. 4. (Note that, even when using a relatively long PVAB, atrial fibrillatory signals are sufficiently rapid that the AF can still be recognized by the device to trigger AMS.) Insofar as AMS is concerned, see, e.g., U.S. Pat. No. 7,062,328 to Levine et al., entitled "System and Method for Providing Improved Specificity for Automatic Mode Switching within an Implantable Medical Device." See, also, U.S. Patent Application 2009/0281587 of Pei, entitled "System and Method for Detecting Hidden Atrial Events for use with Automatic Mode Switching within an Implantable Medical Device."

At step 206, the device engages AMS to switch from the tracking mode to the nontracking mode while (optionally) delivering MSLV CRT pacing and while continuing to use a relatively long PVAB interval. As noted above, depending upon the length of the PVAB interval, the device might not accurately detect high atrial rates during MSLV in a nontracking mode. Also, given the long PVAB associated with MSLV pacing, it can be difficult to distinguish AF from OAT while MSLV pacing continues. As such, in many cases it is preferred that MSLV be deactivated at all rates above the ATAR threshold (i.e. not merely at rates between ATAR and the AMS threshold.) In any case, since the rate exceeds the relatively high AMS threshold, it is assumed that some form of atrial tachycardia is on-going.

The remaining steps of FIG. 3 serve to discriminate or otherwise classify the particular arrhythmia. At step 208, the device tracks the atrial rate and assess the degree of stability (based, e.g., on the cycle length between consecutive AEGMs. Otherwise conventional techniques can be employed to quantify the degree of variation in the atrial intervals so as to assess interval stability. Also, at step 208, the device tracks atrial waveform morphology and assess the degree of similarity of the waveforms. In one example, the device captures each atrial waveform and compares the shape of the waveform against the last atrial waveform to assess the degree of similarity. Otherwise conventional waveform pattern matching techniques can be employed. Another discriminator that may be used to distinguish OAT from Sinus Tachycardia is "sudden onset." Sinus tachycardia gradually accelerates its rate, whereas the various OATs commonly abruptly increase their rate from a normal rhythm to the pathologic rhythm triggered by an atrial premature beat. Hence, the rate of change of the atrial rate can be assessed to distinguish OAT from ST.

In one example, if both atrial rate and morphology are relatively stable over some predetermined number of cycles, the on-going atrial tachycardia is deemed to be an OAT (such as atrial flutter), at step 210. That is, to detect OAT, the atrial rate should be relatively stable and the atrial morphology should also be relatively stable. To determine whether the atrial rate is stable, the device can compare a quantified degree of variation in the atrial intervals against a suitable rate stability threshold. Likewise, to determine whether the atrial morphology is stable, the device can compare a quantified degree of variation in atrial morphology against a suitable morphology stability threshold and/or template that had been previously acquired. If OAT is indicated, the device switches to single-site LV CRT for the duration of the episode of OAT and then resumes MSLV CRT once the episode terminates. Also, at step 210, the device can record suitable diagnostics, generate warnings and/or deliver any therapy that might be appropriate for an OAT (depending upon the capabilities of the device and in accordance with device programming specified by a clinician) to include either ATP and/or high voltage cardioversion therapy.

Conversely, if either the atrial rate or the atrial waveform morphology is relatively instable over the predetermined number of cycles, the on-going atrial tachycardia is instead deemed to be AF, at step 212. If AF is detected, the device continues with MSLV CRT for the duration of the episode of AF in the nontracking mode, then switches back to the tracking mode in accordance with otherwise conventional AMS exit criteria. Also, at step 212, the device can record suitable diagnostics, generate warnings and/or deliver any therapy that might be appropriate for an AF (depending upon the capabilities of the device and in accordance with device programming specified by the clinician.) Such therapy can include delivery of cardioversion shocks to the atria.

It is noted that approximately 90% of atrial tachyarrhythmias are atrial fibrillation whereas 10% are some form of OAT (and the majority of the OATs are atrial flutter). Note also that the various techniques used herein for distinguishing AF, OAT, sinus rhythm, etc., are not restricted for use with MSLV techniques. Indeed, various aspects of the invention are applicable outside the scope of MSLV pacing.

Turning now to FIG. 4, techniques are illustrated for use if the atrial rate is found to be between the lower ATAR threshold and the higher AMS threshold. At step 214, the device switches from MSLV CRT to single-site CRT pacing (i.e. using a single site in the LV in conjunction with a single site in the RV) for a programmable number of cycles while continuing in the tracking mode. This has the effect of temporarily reducing the duration of the PVAB interval. That is, the device is equipped to automatically switch to a shorter PVAB during single site LV pacing as opposed to MSLV pacing. The shorter PVAB will likely reveal additional atrial events that had previously been blanked by the longer PVAB, permitting the detection of the events. At step 216, based on newly detected atrial events, the device confirms that the atrial rate still exceeds the ATAR threshold (set, e.g., to 120 bpm). If not, then there is no atrial tachycardia and MSLV CRT resumes, at step 218.

Assuming that the sensed atrial rate still exceeds the ATAR threshold then, at step 220, the device examines the pattern of atrial depolarization events (i.e. AEGMs) to detect a possible bigeminal pattern arising due to FFRWs. This may determined by comparing the interval between a current AEGM and the next consecutive AEGM'. If AEGM-AEGM' is shorter than AEGM'-AEGM in alternating cycles, then a bigeminal pattern is thereby identified. This is likely due to FFRW oversensing on the atrial channel. (See, for example, U.S. Pat. No. 7,398,123 to Levine, entitled "Methods and Devices for Reducing the Detection of Inappropriate Physiologic Signals to Reduce Misdiagnosis of Normal Rhythms as Tachyarrhythmias." See, also, U.S. Pat. No. 6,810,283 to Suribhotla et al., entitled "Multiple Templates for Filtering of Far Field R-waves"; U.S. Pat. No. 7,437,190 to Hoberman et al., entitled "Cardiac Stimulation Device with Adjustable Blanking Intervals."; U.S. Pat. No. 6,181,968 to Limousin, entitled "Active Implantable Medical Device of the Multisite Type"; and U.S. Pat. No. 4,974,589 to Sholder, entitled "Automatically adjustable blanking period for implantable pacemaker.")

In other words, the high atrial rate that is being observed is actually an artifact of the FFRWs. The true atrial rate is far lower. Hence, the device concludes, at step 222, that the true rhythm is a sinus rhythm and resumes MSLV CRT. (Additionally, depending upon its programming, the device might adjust the sensitivity of the atrial channel in an attempt to avoid further FFRW oversensing. This, however, is not necessarily a good option because true atrial tachyarrhythmias may have a signal amplitude well below that of the intrinsic sinus P wave.)

If a bigeminal pattern is not observed then, at step 224, the device assesses atrial interval stability and atrial waveform stability to distinguishing OAT from other rhythms. That is, at step 224, the device tracks the atrial rate and assesses the degree of rate stability (based, e.g., on AEGM-AEGM cycle length) and also tracks atrial waveform morphology and assess the degree of waveform stability (based, e.g., on the relative similarity of consecutive atrial waveforms.) If the atrial rate and/or morphology are generally consistent with OAT over some predetermined number of cycles, the on-going atrial tachycardia is deemed to be an OAT, at step 226. If OAT is indicated, the device switches to a nontracking mode (i.e. the device engages AMS) and also switches to single-site LV CRT for the duration of the episode of OAT. MSLV CRT resumes once the episode terminates. Insofar as interval instability is concerned, in many patients atrial interval rates may vary by only a few milliseconds from cycle to cycle and so morphology may be a better discriminator. Morphology may be assessed, for example, by comparison against templates representative of OAT and other templates representative of sinus rhythm so as to distinguish OAT from sinus rhythm. Also, at step 226, the device can record suitable diagnostics, generate warnings and/or deliver any therapy that may be appropriate for an OAT. (See FIGS. 5 and 6 for alternative techniques for use following detection of OAT.)

Conversely, if the atrial rate and/or the atrial waveform morphology are generally consistent with sinus rhythm over the predetermined number of cycles, a diagnosis of atrial tachycardia is not confirmed. The rhythm is instead deemed, at step 228, to be a fast sinus rhythm (possibly due to patient exercise) or a slower sinus rhythm wherein (bigeminal) FFRWs are causing the atrial rate to appear higher than it is. (Note that at fast rates FFRWs may result in an apparent stable tachycardia. At slow rates, a bigeminal pattern might appear if the tachycardia is due to FFRW sensing.) In any case, the device resumes MSLV CRT at step 228.

Figure 5:
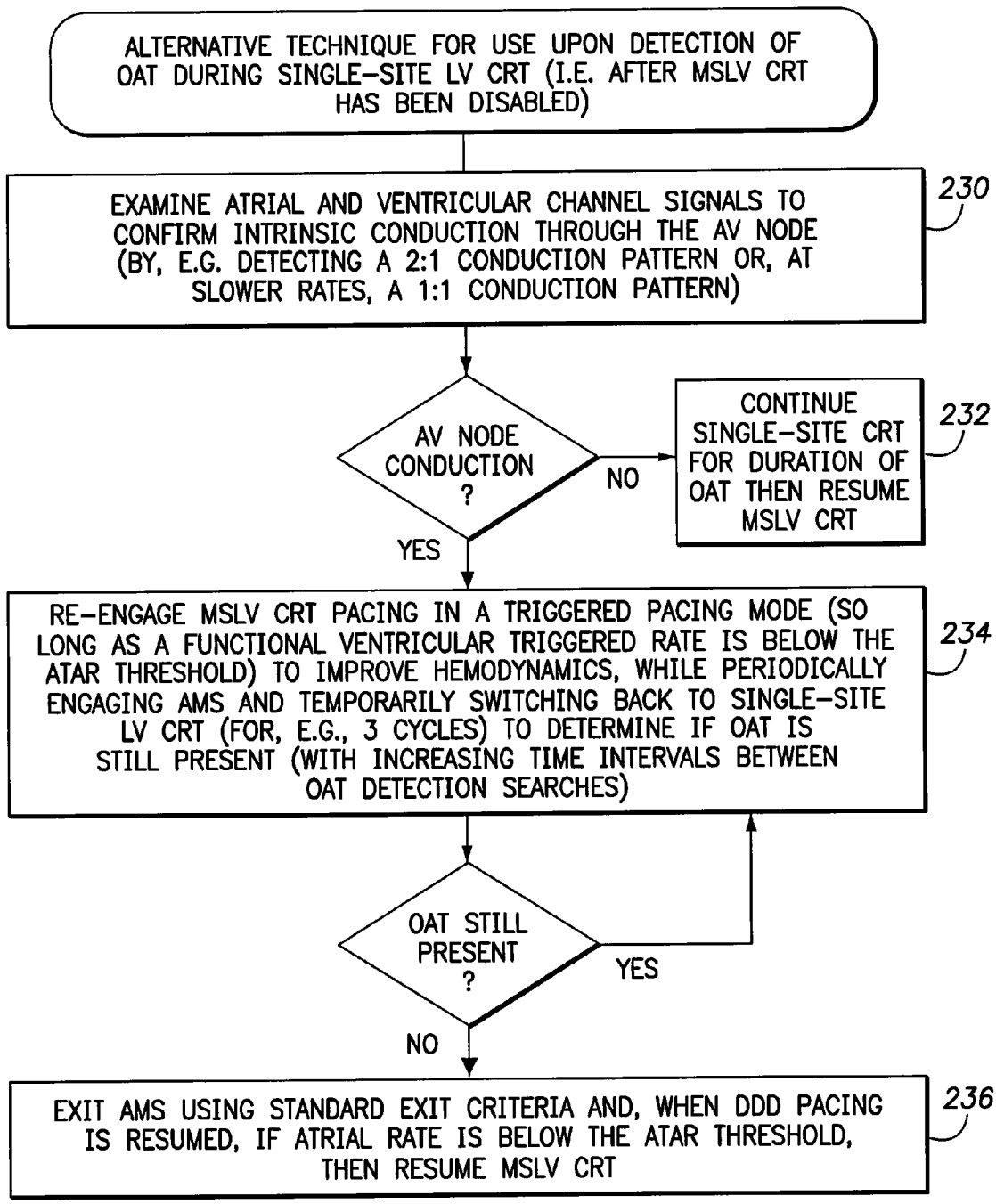
FIG. 5 illustrates an alternative technique, for use as an extension of the technique of FIG. 4 in circumstances where OAT has been detected, wherein MSLV is reengaged and periodic searches are performed to determine whether OAT is on-going.

FIG. 5 illustrates a first alternative technique for use following detection of OAT at step 226 of FIG. 4 (i.e. for use upon detection of OAT during single-site LV CRT after MSLV CRT has been disabled), which provides for periodic OAT searches. In this embodiment, disengagement of MSLV stimulation enables detection of an OAT. That is, if the intrinsic atrial tachyarrhythmia is sufficiently fast to engage AMS converting the pacing mode to a nontracking mode (DDI or VVI) and with this, there is intrinsic conduction through the AV node (in a 2:1 pattern or at the slower rates, 1:1 conduction (with pacing)) such that the pacemaker is totally inhibited for a programmable number of cycles, the device switches to a triggered mode using MSLV stimulation in an effort to optimize hemodynamics during the tachyarrhythmia (assuming the functional ventricular triggered rate is below the ATAR rate.) In this mode, the device periodically (based on time or cycles), suspends MSLV for a programmable number of cycles (with a default of three), to determine whether or not the OAT is still present. The number of cycles between searches is programmable and, preferably, increases with each confirmation that the OAT is still present. For the periodic "look" to determine if the OAT is still present, the first suspension of MSLV may occur after 1 minute, then 2 minutes, then 3 minutes, then 5 minutes, then 10 minutes, then 30 minutes, then 60 minutes, etc. In any case, the periodic search is performed only if the paced rhythm continues to be rapid.

With regard to 1:1 conduction, it is noted that if there is intact conduction the benefits of CRT can be lost and hence the device should be pacing in this setting. Furthermore, insofar as the functional ventricular rate is concerned, given that the AMS threshold is at least 20 bpm greater than the MTR of the device, ventricular triggering cannot occur at the AMS threshold. Another limitation of the triggered rate (in the exemplary embodiment) is that the Ventricular Refractory Period is increased in the triggered mode to minimize the chance of detecting the T-wave and triggering an impulse onto the T-wave (based on an erroneous determination that it is really an R-wave.) The result, called "R on T phenomenon," could result in the induction of VT/VF, which might be catastrophic in a CRT-P device. This technique is summarized by way of FIG. 5. At step 230, the device examines atrial and ventricular channel signals to confirm that there is intrinsic conduction through the AV node (by, e.g. detecting a 2:1 conduction pattern or, at slower rates, a 1:1 conduction pattern.) If intrinsic AV nodal conduction is not occurring, then the device, at step, continues single-site LV CRT for duration of the OAT then resumes MSLV CRT. Assuming, though, that intrinsic AV nodal conduction is confirmed, then the device, at step 234, re-engages MSLV CRT pacing in a triggered pacing mode (so long as the functional ventricular triggered rate is below the ATAR threshold) to improve hemodynamics, while periodically engaging AMS and temporarily switching back to single-site LV CRT (for, e.g., 3 cycles) to determine if OAT is still present (with increasing time intervals between OAT detection searches.) That is, the device periodically searches for OAT. If OAT is not longer occurring then, at step 236, the device exits AMS using standard exit criteria and, when DDD pacing resumes, if the atrial rate is then also below the ATAR threshold, then the device resumes MSLV CRT pacing. The intervals between OAT searches preferably increase so long as OAT continues. This may be achieved by increasing the intervals between searches, as already explained.

Figure 6:
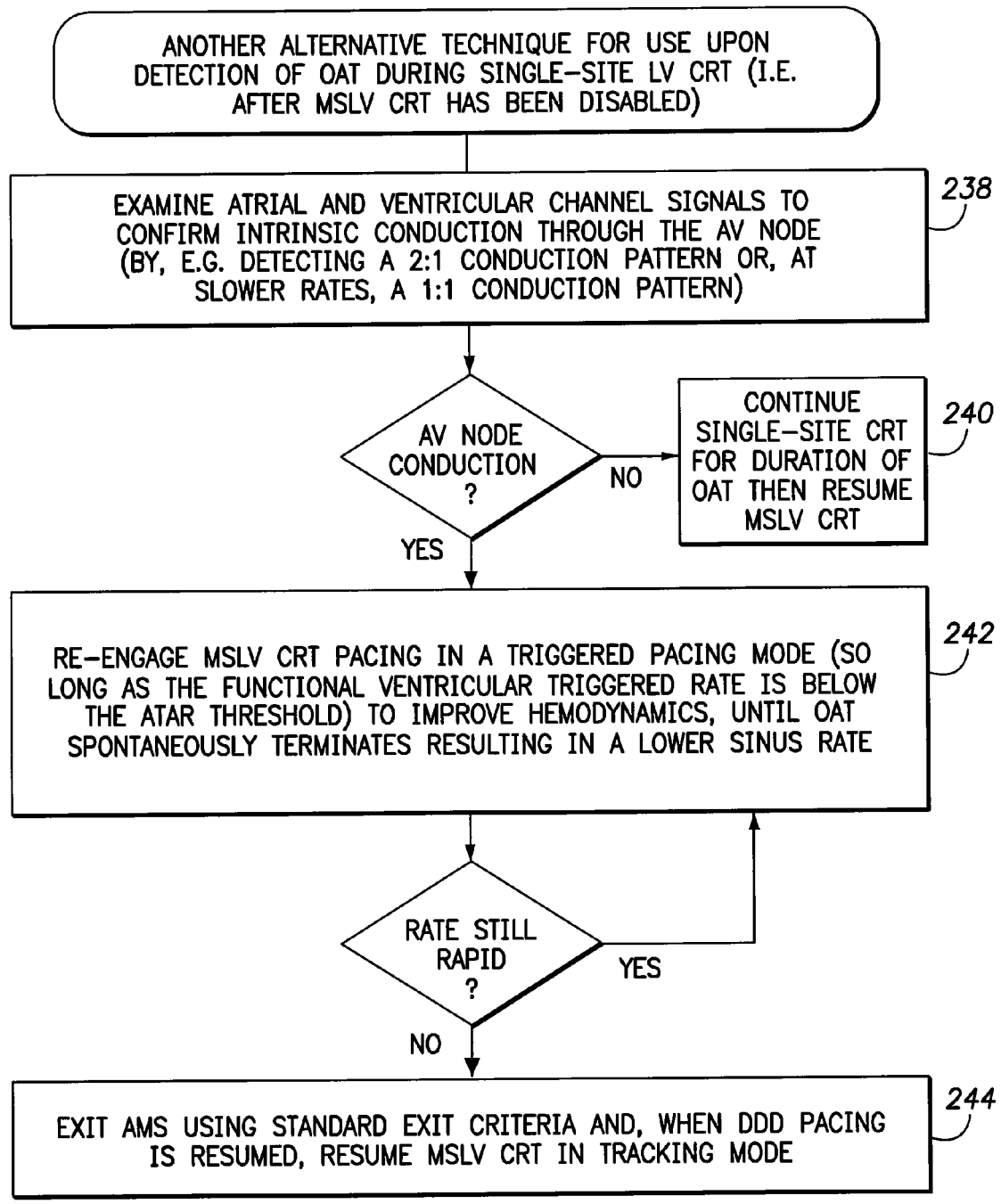
FIG. 6 illustrates another alternative technique, also for use as an extension of the technique of FIG. 4 in circumstances where OAT has been detected, wherein MSLV CRT is reengaged until the OAT spontaneously terminates.

FIG. 6 illustrates a second alternative technique for use following detection of OAT at step 226 of FIG. 4. At step 238, the device examines atrial and ventricular channel signals to confirm intrinsic conduction through the AV node and, as with the technique of FIG. 5, if intrinsic AV nodal conduction is not occurring, the device (step 240) continues single-site LV CRT for duration of the OAT before resuming MSLV CRT. Assuming, though, that intrinsic AV nodal conduction is confirmed, then the device, at step 242, re-engages MSLV CRT pacing in a triggered pacing mode (again so long as the functional ventricular triggered rate is below the ATAR threshold) to improve hemodynamics. MSLV CRT continues in the triggered mode and eventually OAT spontaneously terminates, which results in a substantially lower sinus rate. (In this regard, even though MSLV pacing is delivered, the device can still sense an elevated rate. With an OAT, a rate of 300 bpm might appear to be 150 bpm, and might not be distinguishable from a sinus tachycardia at 150 bpm, but would be above the ATAR. Once the rate falls below the ATAR, the device can detect that OAT has terminated. Note that the device can remain in MSLV even after the OAT terminates, since the device is then functioning in a normal DDD mode.) Upon detection of a rate drop indicative of termination of OAT, the device at step 244, exits AMS using standard exit criteria and, when DDD pacing resumes, if the atrial rate is then also below the ATAR threshold, the device resumes MSLV CRT pacing in a tracking mode.

Thus, various exemplary techniques have been provided that selectively switch from MSLV pacing to single-site LV pacing depending upon whether the atrial rate exceeds one or both of the ATAR threshold and the higher AMS threshold. In the following, a simplified embodiment is summarized wherein the device automatically switches to single-site LV pacing whenever the atrial rate exceeds the ATAR.

Alternative Technique with Single-Site LV Pacing at all Rates Above ATAR

Figure 7:
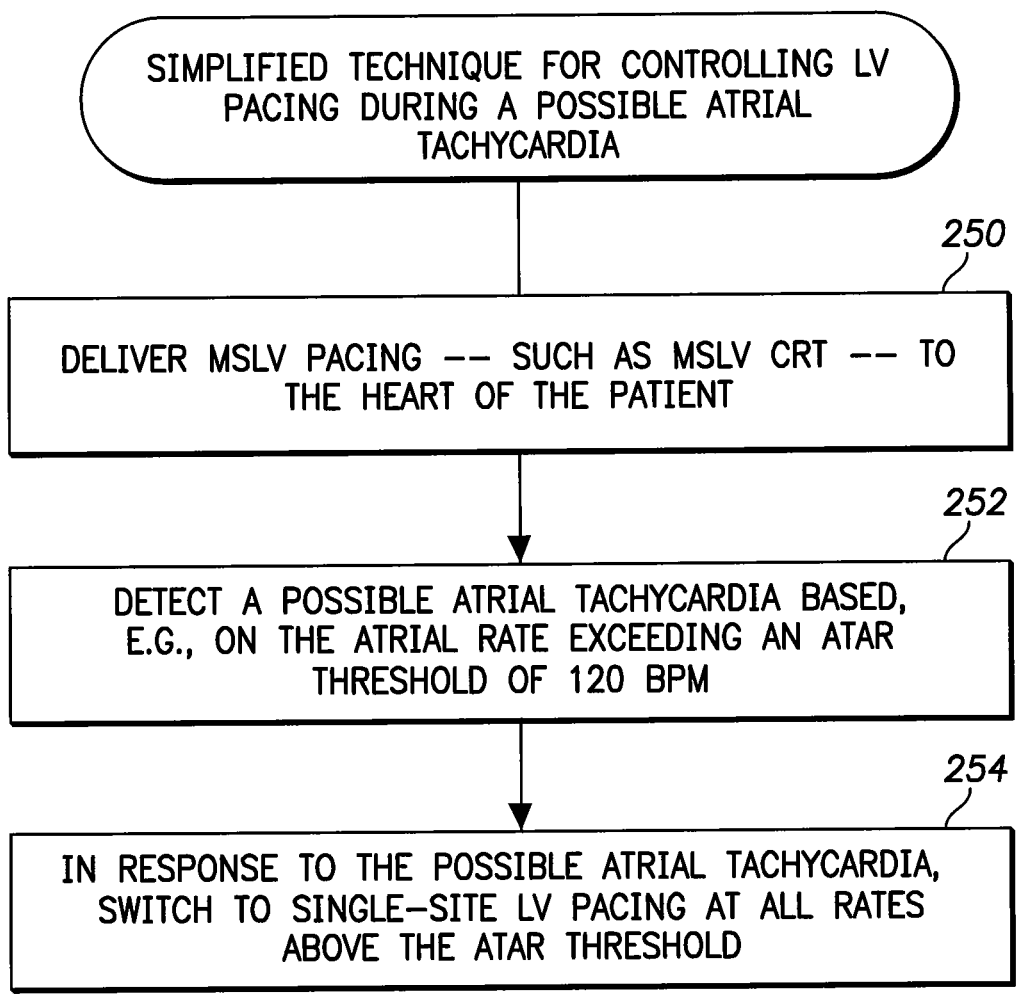
FIG. 7 provides a broad overview of another technique for controlling MSLV CRT that can be performed by the system of FIG. 1, wherein MSLV is disengaged whenever the atrial rate exceeds an ATAR threshold.

Referring to FIG. 7, beginning at step 250, the device delivers MSLV pacing—such as MSLV CRT—to the heart of the patient. At step 252, the device detects a possible atrial tachycardia based, e.g., on the atrial rate (AS-AS) exceeding an ATAR threshold set to 120 bpm. (Note that, since MSLV PVAB is presumably blanking out some AS events, this threshold comparison may instead be regarded as comparing the functional ventricular rate against the ATAR threshold.) In response to the possible atrial tachycardia, the device switches to single site LV pacing at step 254 at all rates above the ATAR threshold. Single-site LV pacing continues until the rate again falls below the ATAR. In this regard, it is believed that there is little hemodynamic benefit from heart rates above 120 bpm in many patients with failing hearts. As such, if the atrial rate exceeds the ATAR threshold, MSLV is automatically disengaged until the atrial rate again falls below the ATAR threshold. This is in contrast with the examples described above wherein, in at least some circumstances, MSLV pacing is delivered at rates above the AMS threshold (which, as noted, is above the ATAR threshold.)

Although not shown in FIG. 7, the device can additionally compare the atrial rate against the higher AMS threshold (as already described) to determine whether to trigger a mode switch. Still further, various techniques (such as those already described) can be employed to discriminate AF from OAT from various sinus rhythms based, e.g. on atrial rate stability and atrial morphology. That is, the technique of FIG. 7 does not preclude these additional/alternative steps or functions.

The purpose of FIG. 7 is instead to broadly illustrate the alternative technique of switching from MSLV to single-site LV pacing whenever the atrial rate exceeds the ATAR threshold.

For the sake of completeness, an exemplary pacer/ICD will now be described, which includes components for performing the functions and steps already described. It should be understood that other implantable medical devices may also be equipped to exploit the techniques described herein, such as dedicated CRT devices and CRT-D devices.

Exemplary Pacer/ICD

Figure 8:
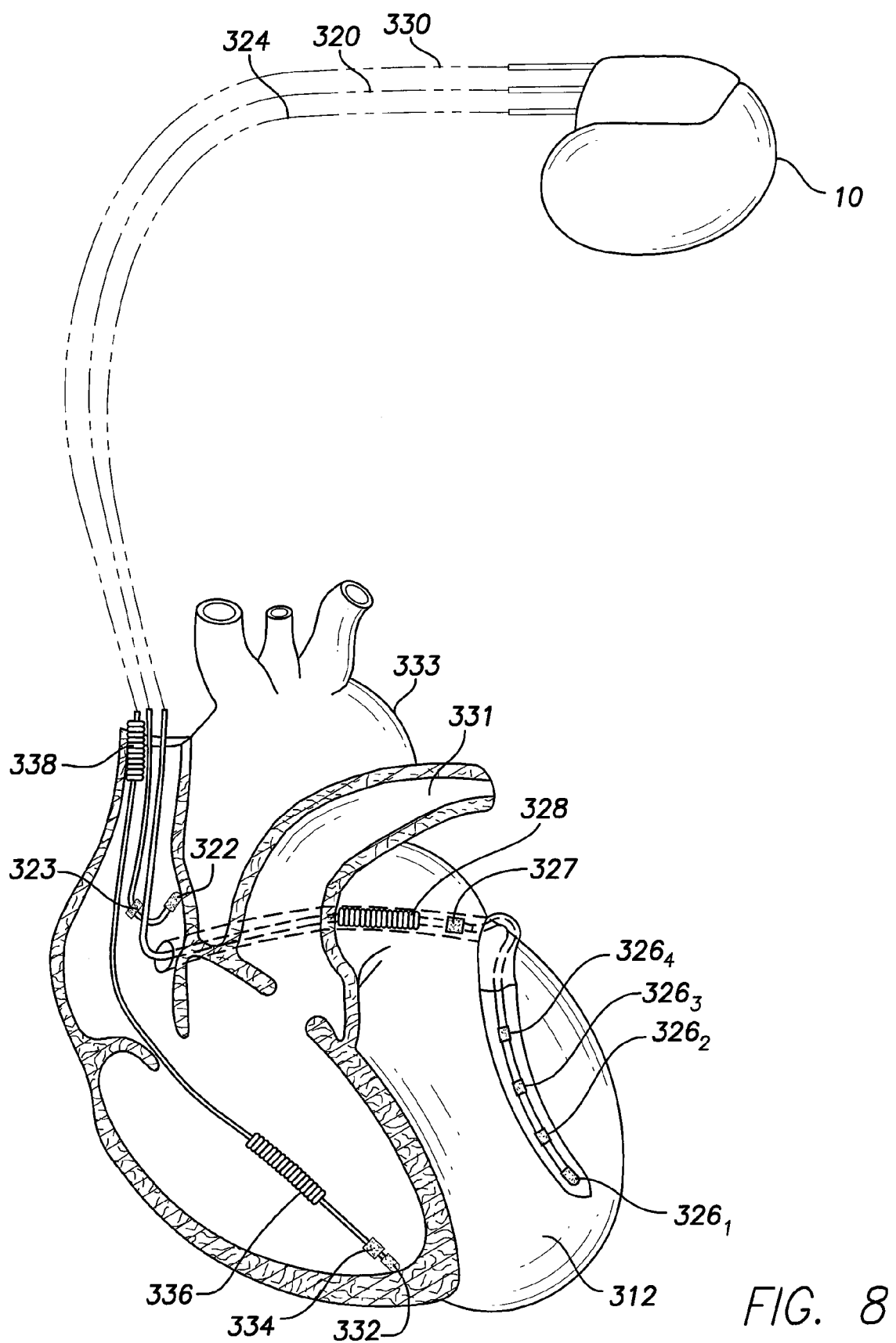
FIG. 8 is a simplified, partly cutaway view illustrating the implantable device of FIG. 1 in electrical communication with at set of leads for delivering multi-chamber stimulation and shock therapy, including a multi-pole LV lead for MSLV pacing.
Figure 9:
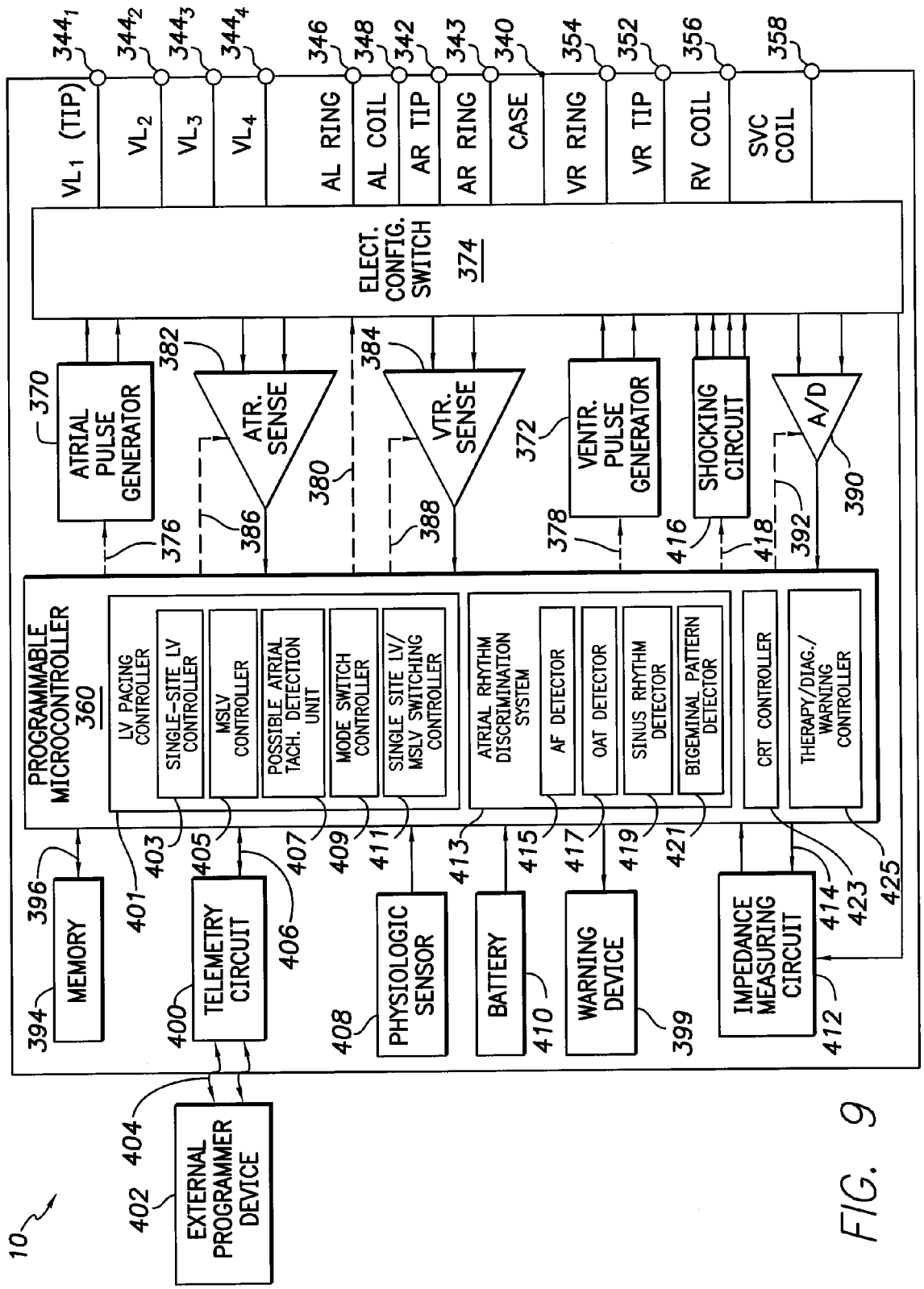
FIG. 9 is a functional block diagram of the multi-chamber implantable stimulation device of FIG. 8, illustrating the basic elements that provide cardioversion, defibrillation and/or pacing stimulation in four chambers of the heart and particularly illustrating components for performing the techniques of FIGS. 2-7.

With reference to FIGS. 8 and 9, a description of an exemplary pacer/ICD will now be provided. FIG. 5 provides a simplified block diagram of the pacer/ICD, which is a dual-chamber stimulation device capable of treating both fast and slow arrhythmias with stimulation therapy, including cardioversion, defibrillation, and pacing stimulation, and also capable of setting and using VV pacing delays, as discussed above. To provide other atrial chamber pacing stimulation and sensing, pacer/ICD 10 is shown in electrical communication with a heart 312 by way of a left atrial lead 320 having an atrial tip electrode 322 and an atrial ring electrode 323 implanted in the atrial appendage. Pacer/ICD 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. Typically, the right ventricular lead 330 is transvenously inserted into the heart so as to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a multi-pole LV lead 324 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 324 is designed to receive atrial and ventricular cardiac signals and to deliver left ventricular pacing therapy using a set of four left ventricular electrodes $326_1$, $326_2$, $326_3$, and $326_4$ (thereby providing a quadra-pole lead), left atrial pacing therapy using at least a left atrial ring electrode 327, and shocking therapy using at least a left atrial coil electrode 328. The $326_1$ LV electrode may also be referred to as a "tip" or "distal" LV electrode. The $326_4$ LV electrode may also be referred to as a "proximal" LV electrode. In other examples, more or fewer LV electrodes are provided. Although only three leads are shown in FIG. 5, it should also be understood that additional leads (with one or more pacing, sensing and/or shocking electrodes) might be used and/or additional electrodes might be provided on the leads already shown, such as additional electrodes on the RV lead.

A simplified block diagram of internal components of pacer/ICD 10 is shown in FIG. 9. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 340 for pacer/ICD 10, shown schematically in FIG. 9, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 further includes a connector (not shown) having a plurality of terminals, 342, 343, $344_1$-$344_4$, 346, 348, 352, 354, 356 and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 322 and a right atrial ring ($A_R$ RING) electrode 343 adapted for connection to right atrial ring electrode 323. To achieve left chamber sensing, pacing and shocking, the connector includes a left ventricular tip terminal ($VL_1$ TIP) $344_1$ and additional LV electrode terminals $344_2$-$344_4$ for the other LV electrodes of the quadra-pole LV lead.

The connector also includes a left atrial ring terminal ($A_L$ RING) 346 and a left atrial shocking terminal ($A_L$ COIL) 348, which are adapted for connection to the left atrial ring electrode 327 and the left atrial coil electrode 328, respectively. To support right chamber sensing, pacing and shocking, the connector further includes a right ventricular tip terminal ($V_R$ TIP) 352, a right ventricular ring terminal ($V_R$ RING) 354, a right ventricular shocking terminal ($V_R$ COIL) 356, and an SVC shocking terminal (SVC COIL) 358, which are adapted for connection to the right ventricular tip electrode 332, right ventricular ring electrode 334, the $V_R$ coil electrode 336, and the SVC coil electrode 338, respectively.

At the core of pacer/ICD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

As shown in FIG. 9, an atrial pulse generator 370 and a ventricular pulse generator 372 generate pacing stimulation pulses for delivery by the right atrial lead 320, the right ventricular lead 330, and/or the LV lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 360 via appropriate control signals, 376 and 378, respectively, to trigger or inhibit the stimulation pulses.

The microcontroller 360 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 382 and ventricular sensing circuits 384 may also be selectively coupled to the right atrial lead 320, LV lead 324, and the right ventricular lead 330, through the switch 374 for detecting the presence of cardiac activity in each of the four chambers of the heart. Accordingly, the atrial (ATR. SENSE) and ventricular (VTR. SENSE) sensing circuits, 382 and 384, may include dedicated sense amplifiers, multiplexed amplifiers or shared amplifiers. The switch 374 determines the "sensing polarity" of the cardiac signal by selectively closing the appropriate switches, as is also known in the art. In this way, the clinician may program the sensing polarity independent of the stimulation polarity. Each sensing circuit, 382 and 384, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 382 and 384, are connected to the microcontroller 360 which, in turn, are able to trigger or inhibit the atrial and ventricular pulse generators, 370 and 372, respectively, in a demand fashion in response to the absence or presence of cardiac activity in the appropriate chambers of the heart.

For arrhythmia detection, pacer/ICD 10 utilizes the atrial and ventricular sensing circuits, 382 and 384, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 390. The data acquisition system 390 is configured to acquire intracardiac electrogram signals, convert the raw analog data into a digital signal, and store the digital signals for later processing and/or telemetry transmission to an external device 402. The data acquisition system 390 is coupled to the right atrial lead 320, the LV lead 324, and the right ventricular lead 330 through the switch 374 to sample cardiac signals across any pair of desired electrodes. The microcontroller 360 is further coupled to a memory 394 by a suitable data/address bus 396, wherein the programmable operating parameters used by the microcontroller 360 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 394 through a telemetry circuit 400 in telemetric communication with the external device 402, such as a programmer, transtelephonic transceiver or a diagnostic system analyzer. The telemetry circuit 400 is activated by the microcontroller by a control signal 406. The telemetry circuit 400 advantageously allows intracardiac electrograms and status information relating to the operation of pacer/ICD 10 (as contained in the microcontroller 360 or memory 394) to be sent to the external device 402 through an established communication link 404. Pacer/ICD 10 further includes an accelerometer or other physiologic sensor 408, commonly referred to as a "rate-responsive" sensor because it is typically used to adjust pacing stimulation rate according to the exercise state of the patient. However, the physiological sensor 408 may further be used to detect changes in cardiac output, changes in the physiological condition of the heart, or diurnal changes in activity (e.g., detecting sleep and wake states) and to detect arousal from sleep. Accordingly, the microcontroller 360 responds by adjusting the various pacing parameters (such as rate, AV delay, VV delay, etc.) at which the atrial and ventricular pulse generators, 370 and 372, generate stimulation pulses. While shown as being included within pacer/ICD 10, it is to be understood that the physiologic sensor 408 may also be external to pacer/ICD 10, yet still be implanted within or carried by the patient. A common type of rate responsive sensor is an activity sensor incorporating an accelerometer or a piezoelectric crystal, which is mounted within the housing 340 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 410, which provides operating power to all of the circuits shown in FIG. 9. The battery 410 may vary depending on the capabilities of pacer/ICD 10. If the system only provides low voltage therapy, a lithium iodine or lithium copper fluoride cell typically may be utilized. For pacer/ICD 10, which employs shocking therapy, the battery 410 should be capable of operating at low current drains for long periods, and then be capable of providing high-current pulses (for capacitor charging) when the patient requires a shock pulse. The battery 410 should also have a predictable discharge characteristic so that elective replacement time can be detected. Accordingly, appropriate batteries are employed.

As further shown in FIG. 9, pacer/ICD 10 is shown as having an impedance measuring circuit 412, which is enabled by the microcontroller 360 via a control signal 414. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 412 is advantageously coupled to the switch 474 so that any desired electrode may be used.

In the case where pacer/ICD 10 is intended to operate as an ICD device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules or higher), as controlled by the microcontroller 360. Such shocking pulses are applied to the heart of the patient through at least two shocking electrodes, and as shown in this embodiment, selected from the left atrial coil electrode 328, the RV coil electrode 336, and/or the SVC coil electrode 338. The housing 340 may act as an active electrode in combination with the RV electrode 336, or as part of a split electrical vector using the SVC coil electrode 338 or the left atrial coil electrode 328 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 7-40 joules), delivered asynchronously (since R-waves may be too disorganized), and pertaining exclusively to the treatment of fibrillation. Accordingly, the microcontroller 360 is capable of controlling the synchronous or asynchronous delivery of the shocking pulses. An internal warning device 399 may be provided for generating perceptible warning signals to the patient via vibration, voltage or other methods.

Insofar as ventricular pacing is concerned, the microcontroller includes an LV pacing controller 401 operative to perform or control the techniques of FIGS. 2-7, described above. The LV pacing controller includes a single-site LV controller 403 operative to control single-site LV pacing (i.e. BiV pacing.) An MSLV pacing controller 405 is operative to control MSLV pacing. A possible atrial tachycardia detector 407 is operative to detect a possible atrial tachycardia based, e.g., on the atrial rate exceeding the ATAR threshold. A mode switch controller 409 is operative to engage AMS based, e.g., on the atrial rate exceeding the AMS threshold. A single site LV/MSLV switching controller is operative to switch between single-site LV and MSLV pacing, in accordance with the techniques described above.

An atrial rhythm discrimination system 413 operates to discriminate various atrial rhythms, such as OAT, AF, and sinus rhythm, using techniques described above. To this end, the discrimination system includes an AF detector 415, an OAT detector 417, a sinus rhythm detector 419 and a bigeminal pattern detector 421.

A CRT controller 423 controls the delivery of CRT (which, as already explained, can be delivered either using single-site LV or MSLV.) A therapy/diagnostics/warning controller 425 controls the delivery of therapy, the recording of diagnostics and/or the generation of warning signals, as might be appropriate in response to various arrhythmias.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use by an implantable cardiac rhythm management device equipped to selectively deliver multi-site left ventricular (MSLV) pacing within a patient, the method comprising:
   delivering MSLV pacing to the heart of the patient within a tracking mode;
   assessing the atrial rate of the patient; and
   comparing an atrial rate against an atrial tachycardia assessment rate threshold (ATAR) and, if the atrial rate exceeds the ATAR threshold, switching from MSLV pacing to single-site pacing to facilitate recognition of organized atrial arrhythmias (OATs).

2. The method of claim 1 further including comparing the atrial rate against an automatic mode switch (AMS) threshold that is higher than the ATAR threshold and, if the atrial rate exceeds the AMS threshold, switching from the tracking mode to a nontracking mode.

3. The method of claim 2 wherein the ATAR threshold is set in the range of 90 to 150 beats per minute (bpm).

4. The method of claim 2 wherein the AMS threshold is set in the range of 170 bpm to 300 beats per minute (bpm).

5. The method of claim 2 wherein a post-ventricular atrial blanking (PVAB) interval is applied to an atrial sensing channel and wherein the PVAB is generally shorter during MSLV pacing than during single-site pacing.

6. The method of claim 2 wherein, while the atrial rate is above the ATAR threshold but not above the higher AMS threshold, the device discriminates the atrial rhythm to distinguish sinus rhythm from an OAT.

7. The method of claim 6 wherein discriminating the atrial rhythm includes:
   examining atrial events detected on an atrial sensing channel to detect a bigeminal pattern indicative of far field R-wave (FFRW) sensing on the atrial channel; and
   in response detection of the bigeminal pattern, identifying the atrial rhythm as sinus rhythm.

8. The method of claim 7 further including confirming the bigeminal pattern indicative of FFRW sensing based on atrial event waveform morphology.

9. The method of claim 7 wherein, in response to the identification of the atrial rhythm as sinus rhythm, switching back to MSLV pacing if the device is currently delivering single-site LV pacing.

10. The method of claim 6 wherein discriminating the atrial rhythm to distinguish sinus rhythm from an OAT includes:
    detecting a degree of stability in atrial event intervals detected on an atrial sensing channel during single-site LV pacing;
    detecting the morphology of atrial events within the atrial sensing channel during single-site LV pacing; and
    distinguishing OAT from sinus rhythm based on one or more of the degree of stability in atrial event intervals and the morphology of the atrial events.

11. The method of claim 10 wherein, in response to the identification of the atrial rhythm as OAT, switching to a nontracking mode while delivering single-site LV pacing.

12. The method of claim 11 further including:
    suppressing pacing and detecting a conduction pattern indicative of intrinsic conduction through the atrioventricular (AV) node of the heart of the patient; and in response to detection of the conduction pattern, switching to MSLV pacing while continuing a nontracking mode.

13. The method of claim 12 further including:
periodically switching back to single-site LV pacing to determine whether OAT is still present and, if not, delivering MSLV pacing.

14. The method of claim 13 wherein periodic returns to single-site LV pacing to determine whether OAT is still present become less frequent over time.

15. The method of claim 12 wherein MSLV pacing continues in the nontracking mode until OAT spontaneously terminates, then MSLV pacing in the tracking mode resumes.

16. The method of claim 2 wherein, while the atrial rate is above the higher AMS threshold, the device discriminates the atrial rhythm based on atrial events detected on an atrial sensing channel to distinguish atrial fibrillation (AF) from an OAT.

17. The method of claim 16 wherein discriminating the atrial rhythm to distinguish AF from an OAT includes:
detecting a degree of stability in atrial event intervals detected on the atrial sensing channel;
detecting the morphology of atrial events within the atrial sensing channel; and
distinguishing OAT from AF based on one or more of the degree of stability in atrial event intervals and the morphology of the atrial events.

18. The method of claim 1 wherein delivering MSLV pacing to the heart of the patient includes delivering cardiac resynchronization therapy (CRT) using a multi-pole LV lead in conjunction with a right ventricular (RV) lead.

19. A system for use by an implantable cardiac rhythm management device equipped to selectively deliver multi-site left ventricular (MSLV) pacing within a patient, the system comprising:
a single-site LV/MSLV pacing controller operative to control the delivery of pacing to the heart of the patient in either a single-site LV mode or an MSLV mode; and
an atrial tachycardia detection system operative to detect a possible atrial tachycardia during MSLV pacing based on an atrial tachycardia assessment rate (ATAR) threshold; with
the pacing controller operative to switch from MSLV pacing to single-site LV pacing while continuing in the tracking mode if the atrial rate exceeds the ATAR threshold.

20. The system of claim 19 further including:
a mode switch controller operative to determine whether a mode switch from the tracking mode to a nontracking mode is appropriate based on an automatic mode switch (AMS) threshold that is set higher than the ATAR threshold.

21. A system for use by an implantable cardiac rhythm management device equipped to selectively deliver multi-site left ventricular (MSLV) pacing within a patient, the system comprising:
means for delivering MSLV pacing to the heart of the patient within a tracking mode;
means for assessing the atrial rate of the patient; and
means for comparing an atrial rate against an atrial tachycardia assessment rate threshold (ATAR) and, if the atrial rate exceeds the ATAR threshold, switching from MSLV pacing to single-site pacing to enable recognition of organized atrial arrhythmias (OATs).

* * * * *